United States Patent
Wakabayashi

(12) 
(10) Patent No.: US 6,352,525 B1
(45) Date of Patent: Mar. 5, 2002

(54) PORTABLE MODULAR CHEST DRAINAGE SYSTEM

(75) Inventor: Akio Wakabayashi, 24 Canyon Fairway Dr., Newport Beach, CA (US) 92660

(73) Assignee: Akio Wakabayashi, Newport Beach, CA (US)

( * ) Notice: Subject to any disclaimer, the term of this patent is extended or adjusted under 35 U.S.C. 154(b) by 0 days.

(21) Appl. No.: 09/401,478

(22) Filed: Sep. 22, 1999

(51) Int. Cl.⁷ .............................. A61M 1/00; A61N 1/30
(52) U.S. Cl. .......................... 604/322; 604/19; 604/317
(58) Field of Search ................................. 604/311–324

(56) References Cited

U.S. PATENT DOCUMENTS

| | | |
|---|---|---|
| 3,628,532 A | 12/1971 | Magrath |
| 3,683,913 A | 8/1972 | Kurtz et al. |
| 3,809,085 A | 5/1974 | Bidwell et al. |
| 3,830,238 A | 8/1974 | Kurtz et al. |
| 4,015,603 A | 4/1977 | Kurtz et al. |
| 4,018,224 A | 4/1977 | Kurtz et al. |
| 4,105,031 A | 8/1978 | Kurtz et al. |
| 4,112,948 A | 9/1978 | Kurtz et al. |
| 4,137,940 A | 2/1979 | Faisandier |
| 4,299,222 A | 11/1981 | Eckenhoff |
| 4,398,910 A | 8/1983 | Blake et al. |
| 4,692,153 A | 9/1987 | Berlin et al. |
| 4,756,501 A | 7/1988 | Quercia et al. |
| 4,784,642 A | 11/1988 | Everett, Jr. et al. |
| 4,941,469 A | 7/1990 | Adahan |
| 4,955,873 A | 9/1990 | Rajlevsky |
| 4,955,874 A | 9/1990 | Farrar et al. |
| 5,044,362 A | 9/1991 | Younes |
| 5,045,075 A | 9/1991 | Ersek |
| 5,211,171 A | 5/1993 | Choromokos |
| 5,300,050 A | 4/1994 | Everett, Jr. et al. |
| 5,318,510 A | 6/1994 | Cathcart |
| 5,370,610 A | 12/1994 | Reynolds |
| 5,458,567 A | 10/1995 | Cathcart |
| 5,507,734 A | 4/1996 | Everett, Jr. et al. |
| 5,578,006 A | 11/1996 | Schön |
| 5,807,313 A | 9/1998 | Delk et al. |

Primary Examiner—Kim M. Lewis
(74) Attorney, Agent, or Firm—Knobbe, Martens, Olson & Bear, LLP

(57) ABSTRACT

A portable drainage system allows patients to ambulate in a hospital or to be discharged to their homes with active suction draining fluids and gases from bodily areas, including sites proximate to surgical procedures. The portable chest tube drainage system includes a vacuum chamber, a vacuum pump housing and a fluid reservoir. These components, in one embodiment, removably connect to the portable drainage system and are disposable. The vacuum pump housing includes a vacuum source, which may comprise a small vacuum pump and one or more removable, replaceable, and/or rechargeable batteries. A vacuum regulating control responsive to user manipulation regulates the vacuum and restricts the vacuum to levels non-injurious to tissues proximate the end of a drainage tube connected to the portable drainage system. A vacuum pressure relief valve incorporated in line maintains the maximal vacuum pressure inside the vacuum chamber below a non-injurious level. A flow meter interposed between the vacuum source and the vacuum chamber indicates an amount of air flow. A one-way valve interposed between the vacuum chamber and fluid reservoir maintains vacuum in the vacuum chamber during removal of the fluid reservoir, and another one-way valve interposed between the vacuum chamber and the vacuum source maintains vacuum in the vacuum chamber during an interruption in the vacuum source. Baffles inside the vacuum chamber separate fluids and gas in the vacuum chamber and direct fluids to the fluid reservoir, while the vacuum pump removes air from the vacuum chamber and exhausts the air to atmosphere by way of the vacuum pump. When filled, the fluid reservoir may be discarded and another fluid reservoir may be connected to continue drainage.

25 Claims, 11 Drawing Sheets

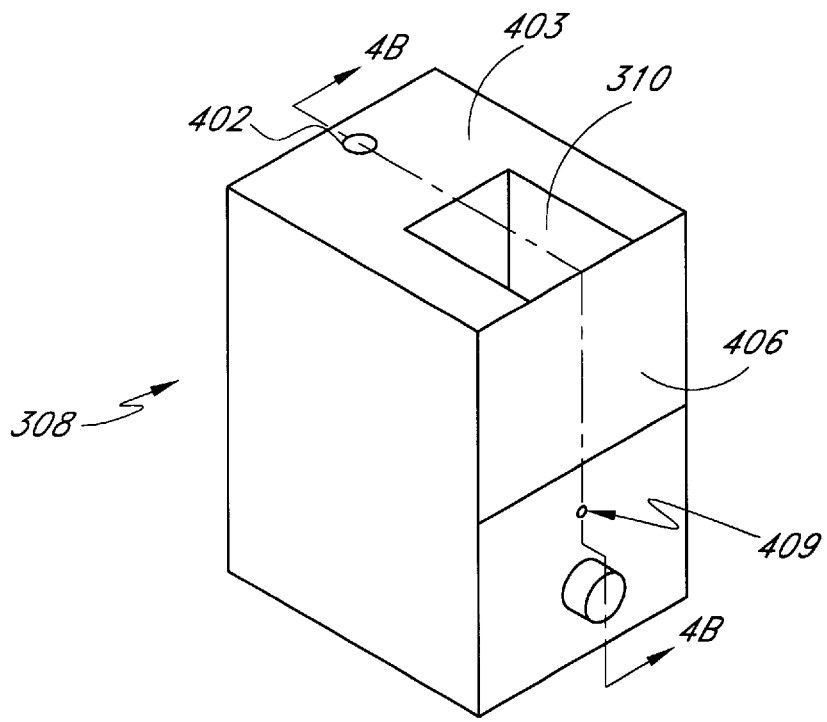
FIG. 4A
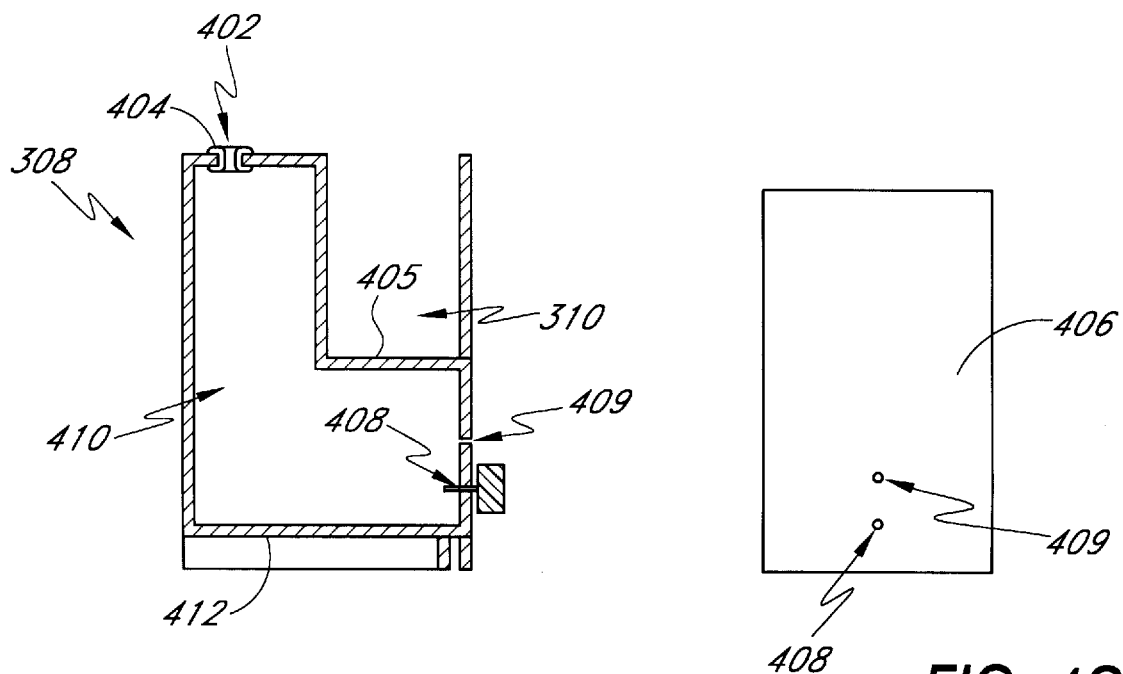
FIG. 4B  FIG. 4C

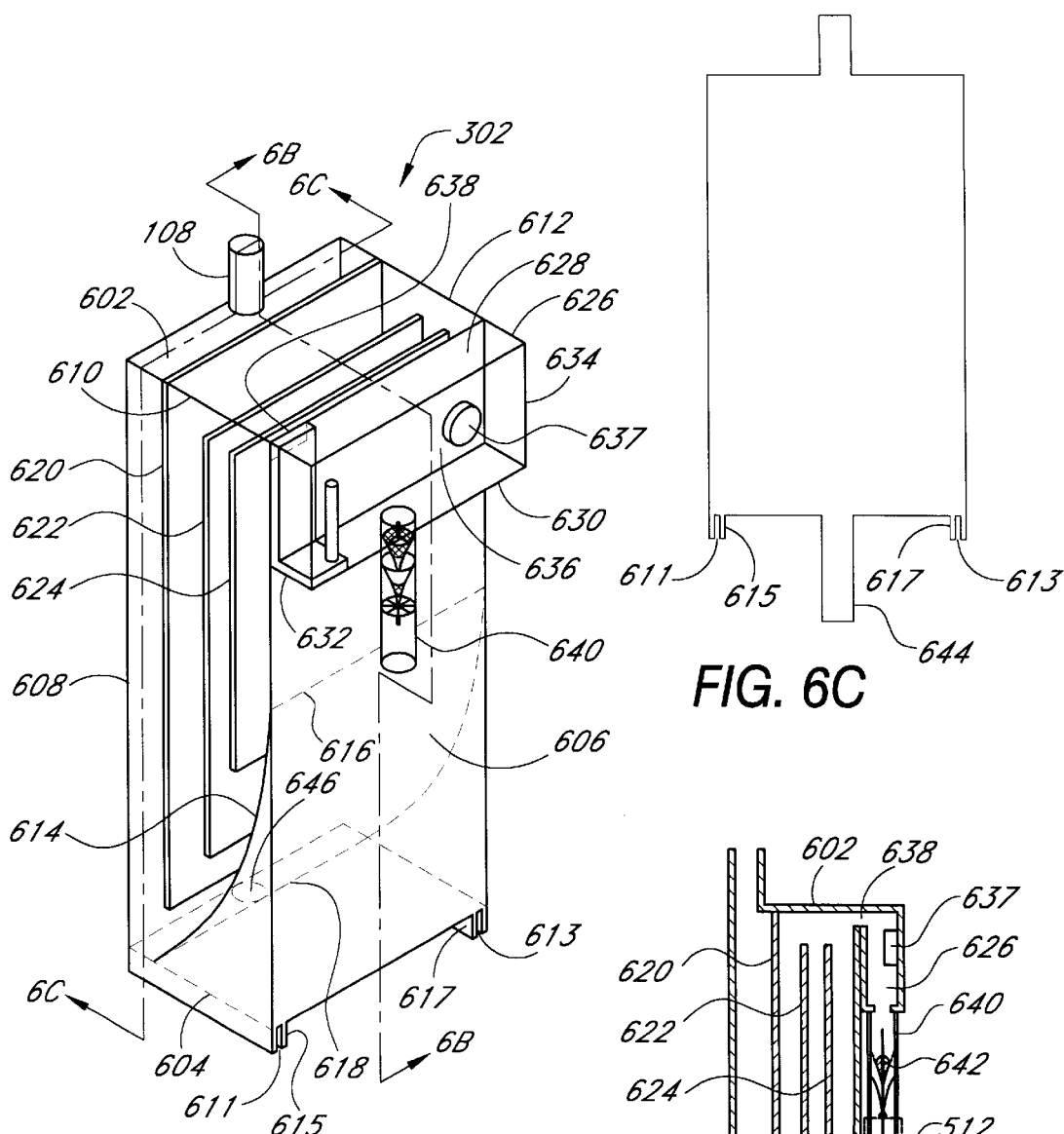
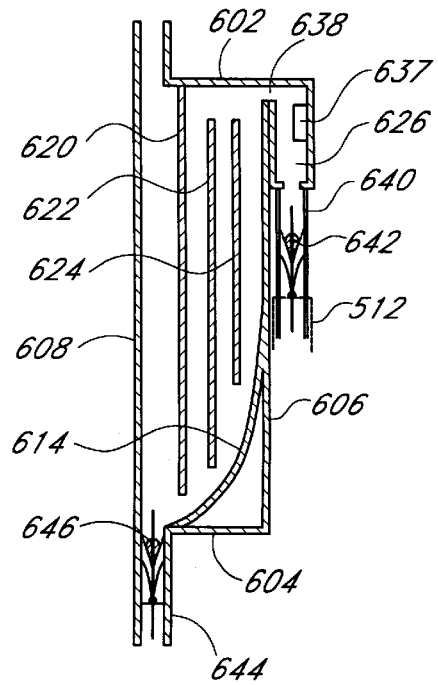
FIG. 6A
FIG. 6B
FIG. 6C

PORTABLE MODULAR CHEST DRAINAGE SYSTEM

BACKGROUND OF THE INVENTION

1. Field of the Invention

The present invention relates to drainage systems and, in particular, to active drainage systems for removal of liquids and gases from the body of an animal, for example, from the pleural cavity of a patient following lung surgery.

2. Description of the Related Art

Early patient drainage systems, for example chest tube drainage systems, utilized a glass bottle and glass tube immersed under water. Vacuum pressure applied to the glass bottle vented fluids from the chest cavity of a patient. The degree of suction was regulated by the height of a column of water inside the glass tube. These chest tube drainage systems required substantial effort from trained personnel to set up and operate, and they required continuous monitoring of the water column and vacuum levels. The tedious initiation and labor-intensive use of such systems limited their availability to hospitals, where patients requiring active chest tube drainage remained until the active drainage was no longer required.

When the number of coronary artery bypass surgeries exploded in the early 1970's, several new types of disposable chest tube drainage systems were introduced on the market. These drainage systems typically connect to either a central vacuum line or to a separate vacuum pump connected to an electrical outlet. While somewhat easier to operate, the availability of these systems generally remained limited to hospitals.

Also, these systems, still used today, are less than ideal for certain types of chestrelated surgeries. For example, existing chest tube drainage systems were designed primarily for cardiac surgeries, and not for pulnonary or lung-related surgeries. Since the number of lung-related surgeries is substantially less than the number of cardiac surgeries, very little research and development has been directed to the design of commercial drainage systems for lung-related surgeries or other types of medical procedures presenting recovery concerns which differ from those related to cardiac surgeries.

For example, following cardiac surgery, physicians are concerned with the precise amount of bleeding as well as the recovery of the patient's blood which is often given back to patients. In contrast, however, during a patient's recovery from lung surgery, a surgeon is generally more concerned about the presence and persistence of air leaks in the patient's lung(s) than the amount of bleeding from the surgery. Such air leaks from lungs, especially emphysematous lungs, can persist for days or even weeks, and must be carefully monitored. Following lung surgery, the fluid drained from a patient is typically a mixture of blood and lymph and gases, and current protocols do not include giving that mixture back to the patient.

One problem with existing drainage systems is that the vacuum generated by a central vacuum line or an AC-powered portable suction pump can be quite powerful. To prevent injury from excessive vacuum force, existing drainage systems use pressure regulating means such as a water column or a dry pressure regulator. Despite these safety features, bodily tissue, such as lung tissue, may be injured if it is sucked against the chest tube due to excessively high vacuum power of the central vacuum line.

Another problem is that drainage systems that are now commercially available have been designed only for in-patient (hospital-based) use. Even in the hospital, existing drainage systems substantially impair patient mobility. Moreover, the complexity of these systems requires constant in-service training of nurses and technicians to operate them.

Surgical patients often require drainage treatments for extended periods of time following surgical procedures. For example, when air leak after lung surgery persists, chest tubes, which remain in the patient's chest following the surgery, often need to be suctioned for many days. If the amount of air leak is small and the patient's general condition is stable, such a patient may now be discharged home with a chest tube connected to a one-way valve, such as Heimlich valve. Such one-way valve systems, however, use passive drainage means, which frequently fail to prevent collapsing of the lung, and, therefore, the utility of such systems is very limited.

There is now a great need and demand in the medical community for an active portable drainage system, which will allow medically stable patients go home soon after surgery with their chest tubes continuously and safely vented during recovery. Not only would the medical expenses for these patients be markedly reduced, but also they would be permitted to recover in the more familiar and comfortable, and less stressful, environment of their own homes.

SUMMARY OF THE INVENTION

One aspect of the present invention is a portable active drainage system. The system comprises (1) a vacuum source creating a vacuum; (2) a vacuum chamber having a drainage tube port, a vacuum port and a reservoir port, the vacuum chamber connected to the vacuum source through the vacuum port to apply the vacuum to vent fluid from an animal through the drainage tube port when the drainage tube port is connected to a drainage tube extending from a location inside the animal; and (3) a reservoir having an input port connected to the reservoir port, the reservoir receiving vented liquid through the input port, the reservoir configured in combination with the vacuum source and the vacuum chamber to provide a self-contained and transportable unit. In preferred embodiments of this system, a further advantageous aspect exists wherein the vacuum chamber separates gas and liquid from the vented fluid. Another advantageous aspect of this system further comprises a flow meter indicating a flow quantity. A further advantageous aspect of the system is one wherein the flow quantity corresponds to a leak in at least one lung of the animal. Still another advantageous aspect of the system is one wherein the vacuum source includes a vacuum pump and a power source. A still further advantageous embodiment of the system is one wherein the vacuum source is substantially enclosed within a vacuum pump housing. Another advantageous aspect of the system is one wherein the power source includes at least one battery and wherein the vacuum pump operates from electrical current provided by the at least one battery. A further advantageous embodiment of the system is one wherein the power source includes a power converter converting current from a standard electrical outlet to an electrical current suitable to power said vacuum pump and wherein the power converter is configured to be connected to a standard electrical outlet. Yet another advantageous embodiment of the system is one wherein the battery is a rechargeable battery, and wherein the power source includes a battery recharger configured to charge the battery and provide current suitable to power the vacuum pump. Another advantageous embodiment of the system is one wherein the vacuum chamber includes at least one baffle separating liquid and gas from the vented fluid. In yet another advantageous embodiment, the system is one wherein the reservoir port includes a one-way valve, the one-way valve maintaining the vacuum inside the vacuum chamber during removal or replacement of the reservoir. Still another advantageous embodiment of the system is one wherein the vacuum source moves gases from the vacuum chamber into the atmosphere. A still further advantageous embodiment is one wherein the vacuum port includes a one-way valve, the one-way valve maintaining vacuum inside the vacuum chamber during an interruption in the vacuum source. In another advantageous embodiment, the system further comprises a regulating control that regulates the vacuum. A further advantageous aspect of the system is one wherein a maximum vacuum permitted by the regulating control is insufficient to injure living tissues exposed to the maximum vacuum. In yet another advantageous embodiment, the system further comprises a vacuum relief valve regulating the vacuum. In a still further advantageous embodiment, the system further comprises a tilt switch detecting tilt along at least one axis and providing a tilt signal when the amount of tilt exceeds a predetermined threshold. In a further advantageous embodiment, the system further comprises a tilt alarm responding to said tilt signal by generating an audible sound. In yet a further advantageous embodiment, the system further comprises a tilt alarm responding to the tilt signal by generating a visible indication of a tilt condition. In another advantageous embodiment, the system further comprises a second drainage tube port, wherein fluid is vented from the animal through the second drainage tube port when the second drainage tube port is connected to a second drainage tube extending from a location inside the animal.

Another aspect of the present invention is a method for draining fluid from an animal. The method comprising the steps of (1) inserting a first end of a first drainage tube into an animal; (2) connecting a second end of the first drainage tube to a first drainage tube port of an active drainage system, the animal supporting the weight of the active drainage system, the active drainage system including a source of electricity and producing vacuum from the electricity; and (3) applying the vacuum to the second end of the first drainage tube. Preferred embodiments of the method exist, and, in one advantageous aspect, the method is one wherein the animal ambulates using its natural mode of transportation during the application of the vacuum. In a further preferred embodiment, the method comprises the further step of venting fluid from the animal into the active drainage system through the first drainage tube. In another preferred embodiment, the method comprises the further step of collecting liquid from the animal in a reservoir of the active drainage system. In still another preferred embodiment, the method comprises the further step of separating gas and liquid from the vented fluid. A further advantageous aspect of the method is one wherein the animal is a human. Another advantageous embodiment of the method comprises the further steps of inserting a first end of a second drainage tube into the animal; connecting a second end of the second drainage tube to a second drainage tube port of the active drainage system; and applying vacuum to the second end of the second drainage tube. Still another advantageous embodiment of the method comprises the further steps of inserting a first end of a second drainage tube into the animal; and connecting a second end of the second drainage tube to a first drainage tube port of a second active drainage system, the animal supporting the weight of the second active drainage system.

Yet another aspect of the present invention is a method for draining fluid from an animal. The method comprises the steps of (1) inserting a first end of a first drainage tube into an animal; (2) connecting a second end of the first drainage tube to a first drainage tube port of an active drainage system, the animal supporting the weight of the active drainage system; (3) applying vacuum to the second end of the first drainage tube, the vacuum generated by the active drainage system; (4) venting fluid from the animal; and (5) separating gas and liquid from the vented fluid. Further advantageous preferred embodiments exist, and one preferred embodiment of the method comprises the further step of exhausting the gas into the atmosphere during the application of the vacuum. Another advantageous embodiment of the method comprises the further steps of tilting the active drainage system at least a predetermined number of degrees along an axis; and responding to the tilting by activating a perceivable alarm.

Still another aspect of the present invention is a method for draining fluid from a mammal. The method comprises the steps of (1) inserting a chest tube into the pleural cavity of a mammal so that a first end of the chest tube is proximate to a lung; (2) connecting a second end of the chest tube to an active drainage system; (3) applying a vacuum from the active drainage system to the chest tube; (4) regulating the vacuum to correspond to an air leak in the lung; and (5) venting fluid from a location proximate to the lung while the mammal ambulates and while the mammal supports the weight of the active drainage system. Further advantageous preferred embodiments exist, and one further advantageous preferred embodiment of the method is one comprising the further step of determining an amount of air leak in the lung with a flow meter of the active drainage system. Another advantageous embodiment of the method comprises the further step of regulating the vacuum so that it does not harm living tissue proximate to the first end of the chest tube. Another advantageous embodiment of the method is one wherein the mammal is a human.

Another aspect of the present invention is a portable active drainage system. The system comprises (1) vacuum generating means for generating a vacuum; (2) power source means for supplying an electric current to the vacuum generating means; (3) venting means for directing vacuum from the vacuum generating means to a drainage tube extending from a location inside an animal and for venting fluid from the animal; (4) separating means for separating liquid and gas from the vented fluid; (5) collection means for collecting the separated liquid; and (6) support means permitting the animal to support the weight of the portable active drainage system while ambulating.

BRIEF DESCRIPTION OF THE DRAWINGS

These and other features and advantages of the invention will become more apparent upon reading the following detailed description and upon reference to the accompanying drawings, in which;

FIG. 4A illustrates a representation of a perspective view of the vacuum pump housing in one embodiment of the present invention;

FIG. 4B illustrates a cross-sectional view of the vacuum pump housing in one embodiment of the present invention;

FIG. 4C illustrates a frontal view of a vacuum pump housing in one embodiment of the present invention;

FIG. 6A illustrates a representation of a perspective view of a vacuum chamber in accordance with an embodiment of the present invention;

FIG. 6B illustrates a representation of a cross-sectional side view of a vacuum chamber in accordance with an embodiment of the present invention;

FIG. 6C illustrates a representation of a rear view of a vacuum chamber in accordance with an embodiment of the present invention;

DETAILED DESCRIPTION

The embodiment of the invention described herein may be used in connection with a human patient and in the context of lung surgery. However, it is contemplated that the present invention is not limited to humans or to lung-related surgeries, and may be advantageously applied to other animals in contexts not limited to lung-related medical procedures.

Figure 1:
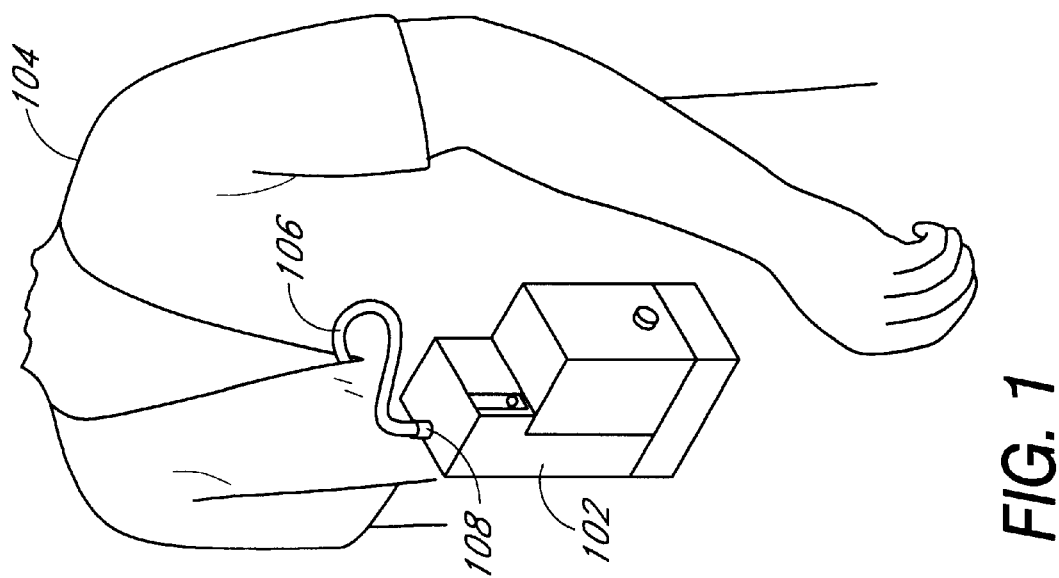
FIG. 1 illustrates a representation of a patient moving about and using a chest tube drainage system in accordance with an embodiment of the present invention.

FIG. 1 illustrates a representation of a patient moving about and using a chest tube drainage system 102 in accordance with an embodiment of the present invention. The chest tube drainage system 102 is worn about the body of a patient 104, advantageously permitting the patient 104 to walk freely about while a chest tube 106 is actively vented by the drainage system 102.

The chest tube 106 extends from inside the patient's 104 body proximate to the site of a surgical operation (not shown) to connect to a drainage tube port 108 of the drainage system 102. In the embodiment shown in FIG. 1, one or more batteries (not shown) provide power to the chest tube drainage system 102.

A strap 110 about the shoulders and torso of the patient 104 holds the chest tube drainage system 102 in an operable position relative to the patient's 104 body. The strap 110 may be adjustable to fit patients of different sizes, may have padded and/or elastic areas for comfort, and may removably attach to the chest tube drainage system using any one of a number of clip-on type arrangements. In an alternative embodiment, the chest tube drainage system 102 could attach to or be integrated with specially configured clothing such as, for example, fitted into an appropriately sized and shaped pocket (not shown).

Figure 2:
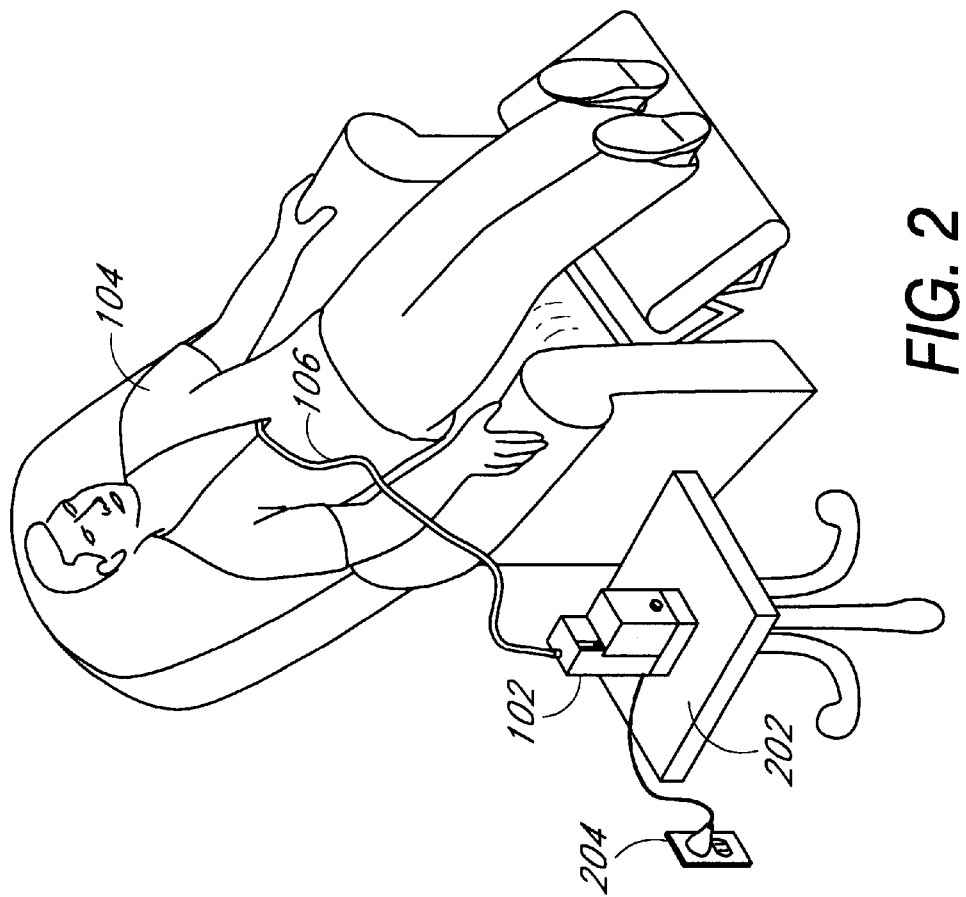
FIG. 2 illustrates a representation of a patient at rest using a chest tube drainage system in accordance with an embodiment of the present invention.

FIG. 2 illustrates a representation of a patient 104 at rest using a chest tube drainage system in accordance with an embodiment of the present invention. The patient 104 rests in a reclining position. The chest tube drainage system 102 rests on a surface 202 while actively venting the chest tube 106. Advantageously, as the patient 104 is not actively moving about, power from a standard AC outlet 204 provides power for the drainage system 102 while recharging the batteries of the drainage system 102.

Advantageously, the entire drainage system is made completely portable by combining a vacuum pump, a power source, a vacuum chamber, and a collection unit into a single compact unit. The portable but highly effective unit provides treatment advantages not previously possible. For example, upon recovery from anesthesia following surgery, patients may immediately commence ambulatory therapy, arms free and without assistance of others, and/or may even be discharged from the hospital with uninterrupted drainage therapy.

The drainage system of the present invention also advantageously provides scalable drainage capacity. Following some surgical procedures, a patient may require more than one chest tube. Often, two or more chest tubes may need to be actively vented. In one example, a patient may have one or more air leaks requiring removal of over three (3) liters per minute of air. In accordance with the present invention, multiple chest tube drainage systems 102 may be used to vent multiple chest tubes 106. In another embodiment, a single chest tube drainage system 102 includes multiple drainage tube ports, those unused being sealed with, for example, a snug fitting rubber cap.

The drainage system of the present invention further advantageously separates liquids and gases from vented fluid. As used herein, fluid refers to any liquids and/or gases. The drainage system disperses gases into the atmosphere and collects vented liquids in a disposable collection reservoir.

Figure 3:
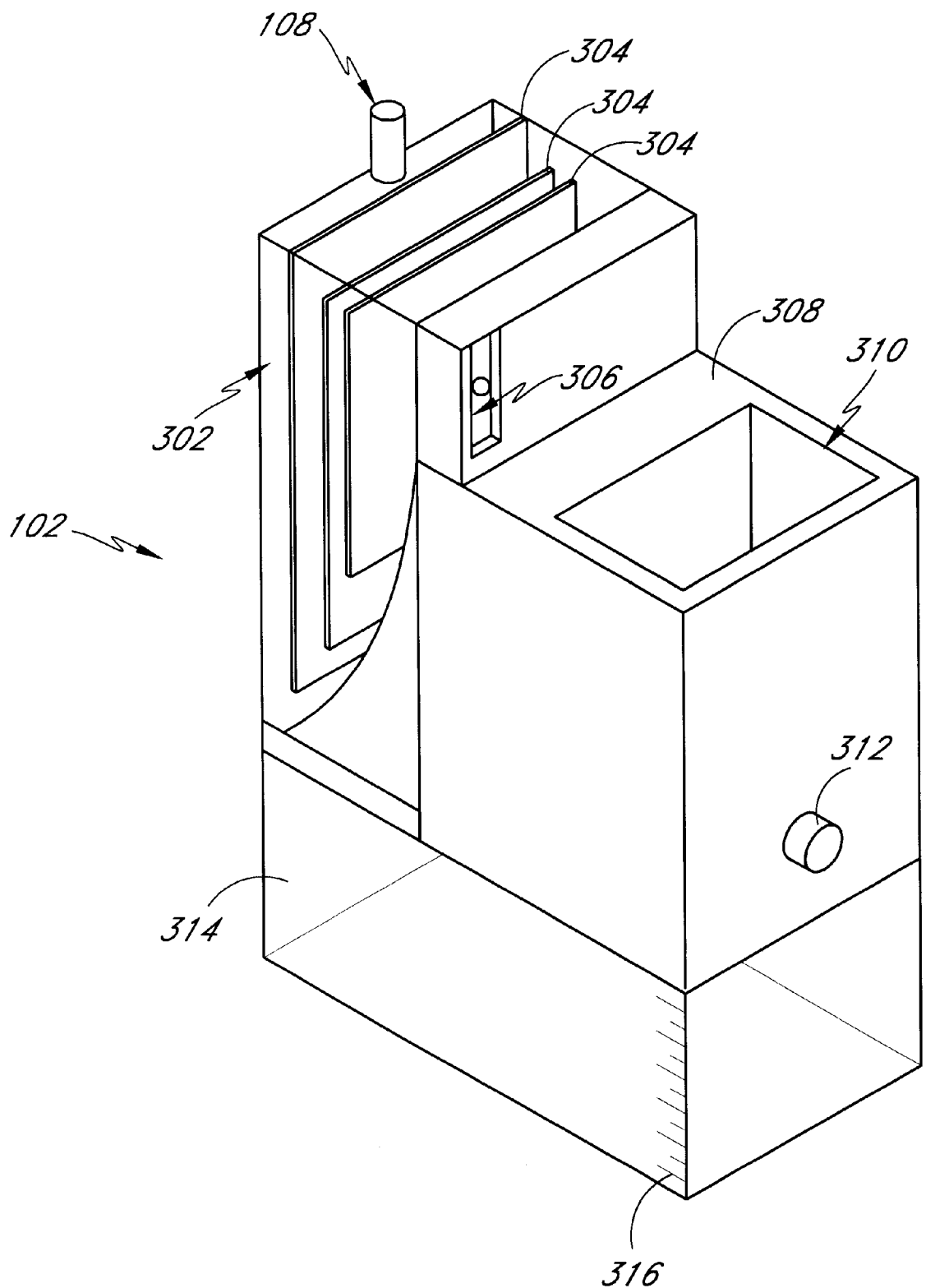
FIG. 3 illustrates a perspective view of a chest tube drainage system in accordance with an embodiment of the present invention.
Figure 4D:
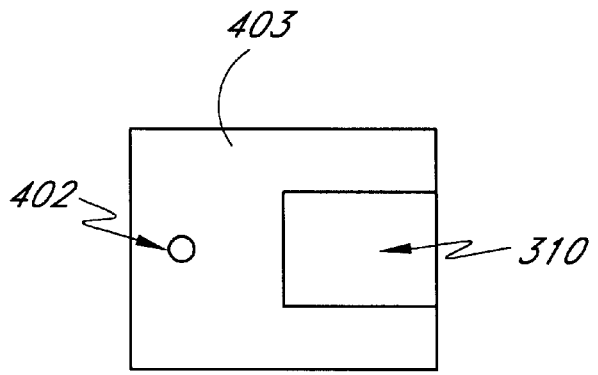
FIG. 4D illustrates a view from the top of the vacuum pump housing in one embodiment of the present invention.
Figure 4E:
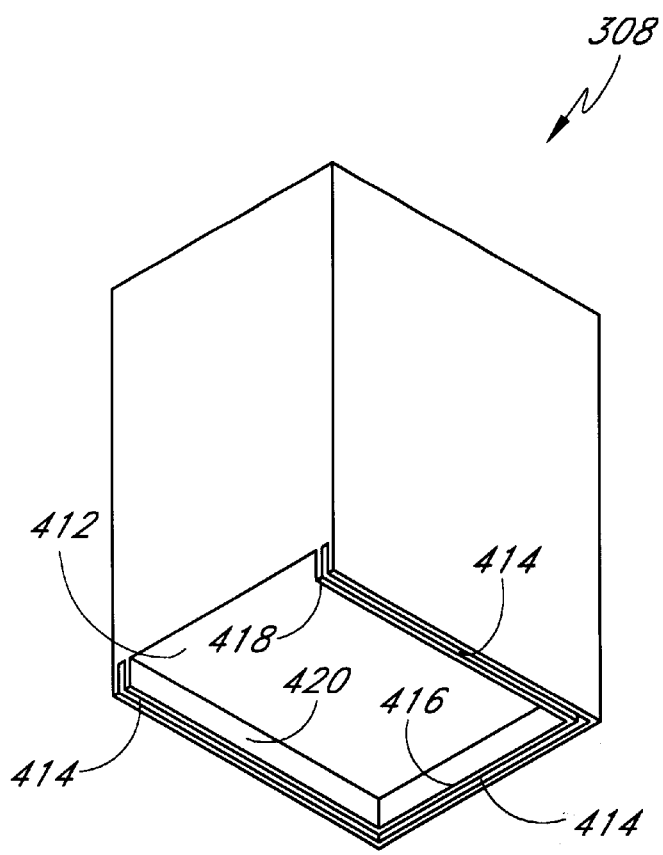
FIG. 4E illustrates a representation of a perspective view from the bottom of the vacuum pump housing in one embodiment of the present invention.
Figure 5A:
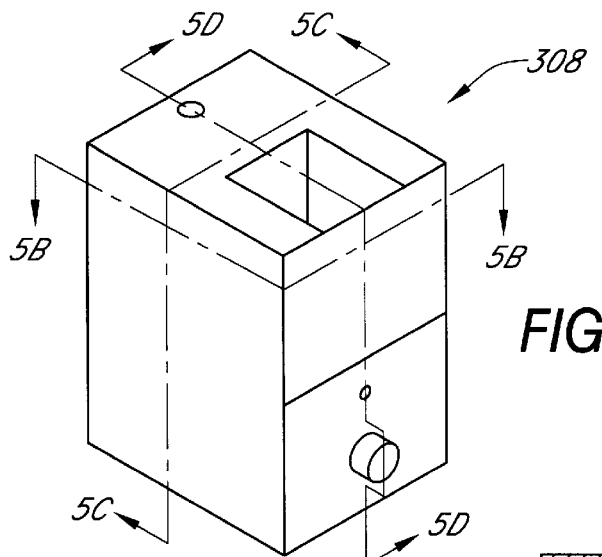
FIG. 5A illustrates a representation of a perspective view of a vacuum pump housing in accordance with an embodiment of the present invention.
Figure 5B:
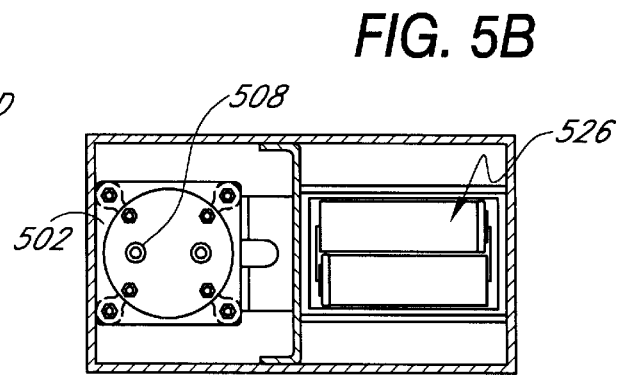
FIG. 5B illustrates a representation of a top down view of an arrangement of a vacuum pump and a battery pack in a vacuum pump housing in accordance with an embodiment of the present invention.
Figure 5C:
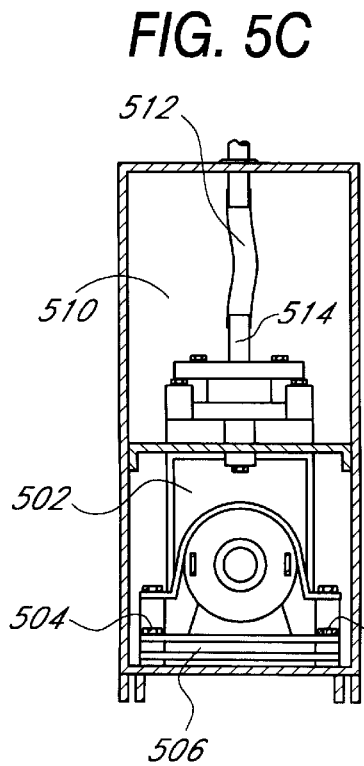
FIG. 5C illustrates a representation of a frontal view of an arrangement of a vacuum pump within a vacuum pump housing in accordance with an embodiment of the present invention.
Figure 5D:
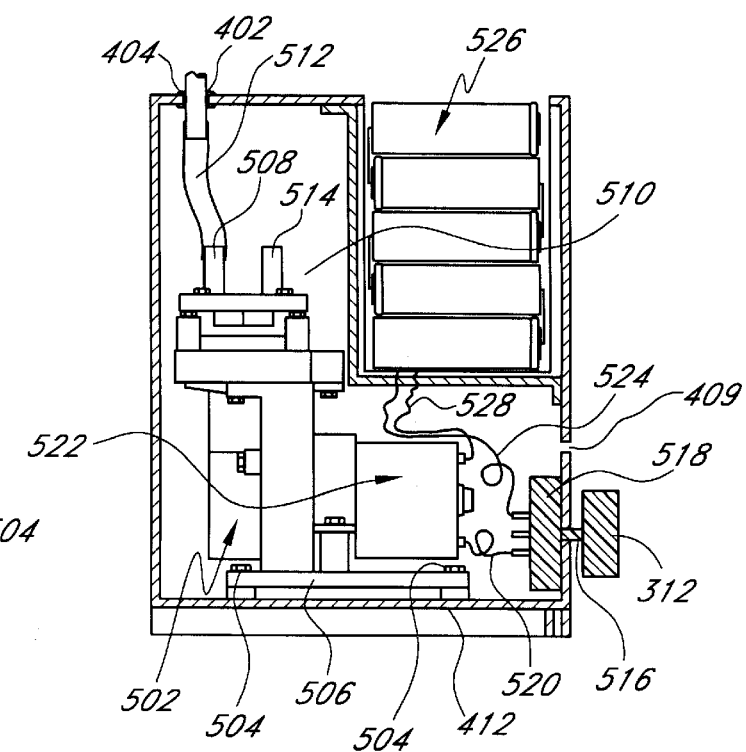
FIG. 5D illustrates a representation of a side view of an arrangement of a vacuum pump and a battery pack in a vacuum pump housing in accordance with an embodiment of the present invention.
Figure 7A:
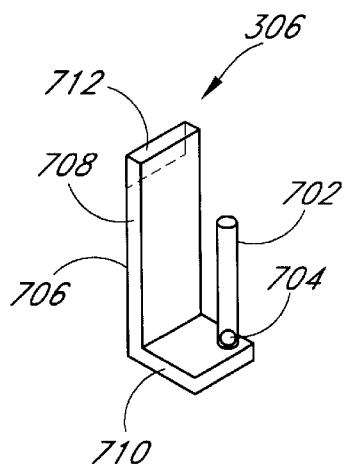
FIG. 7A illustrates a representation of a perspective view of a flow meter in accordance with one embodiment of the present invention.
Figure 7B:
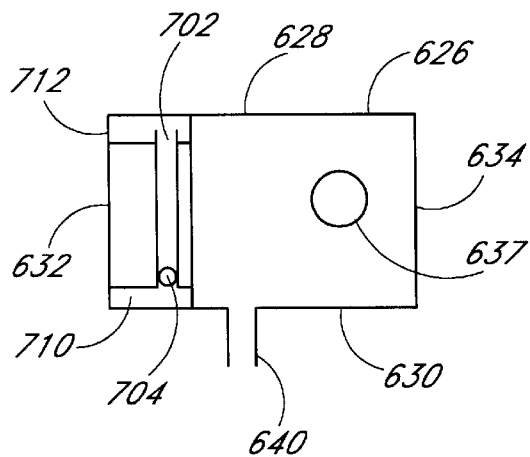
FIG. 7B illustrates a representation of a frontal view of the arrangement of a flow meter relative to a flow meter housing in accordance with an embodiment of the present invention.
Figure 7C:
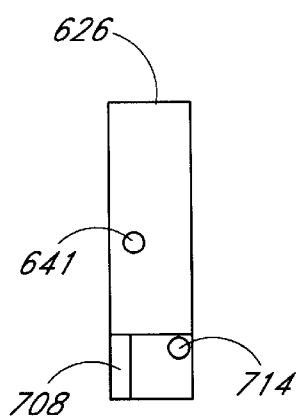
FIG. 7C illustrates a representation of a top down view of an arrangement of a flow meter relative to a flow meter housing in accordance with an embodiment of the present invention.
Figure 7D:
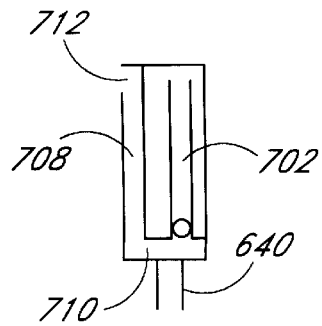
FIG. 7D illustrates a representation of a side view of a flow meter arranged in a flow meter housing in accordance with an embodiment of the present invention.
Figure 7E:
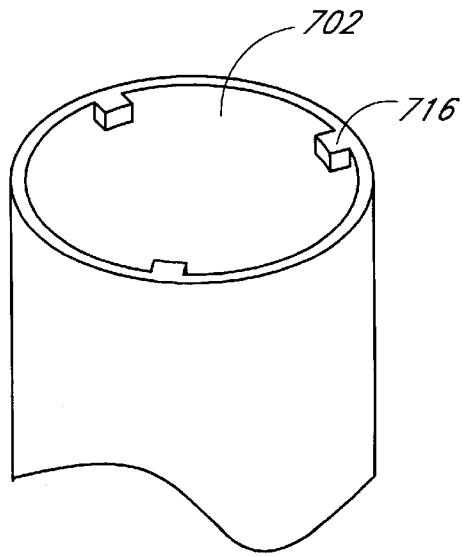
FIG. 7E illustrates retaining members holding a floating ball within a tube of a flow meter in accordance with an embodiment of the present invention.

FIG. 3 illustrates a perspective view of a chest tube drainage system in accordance with one embodiment of the present invention. In one embodiment, the chest tube drainage system 102 includes three main components: a vacuum chamber 302, a vacuum pump housing 308, and a collection reservoir 314. The vacuum chamber 302, the vacuum pump housing 308, and the collection reservoir 314 are removably connected to the chest tube drainage system 102. Each component of the drainage system 102 is generally disposable, being made of plastic having a thickness approximately in the range of 0.01 to 0.25 inches. Of course, other widths of plastic and other materials may be used without departing from the spirit of the invention.

The drainage tube port 108 connects the vacuum chamber 302 to the chest tube 106 (FIG. 1). A flow meter 306 is interposed between the vacuum chamber 302 and the vacuum pump housing 308 to indicate the amount of air flow. In the context of a patient recovering from lung-related surgery, the flow meter 306 advantageously indicates an amount of air leak from the patient's lung(s). In a preferred embodiment, the flow meter 306 is fixedly attached to the vacuum chamber 302. It will be appreciated that the flow meter could alternatively be removably attached or integrally formed with the vacuum chamber 302, or could be configured as a separate component removably attachable to both the vacuum chamber 302 and the vacuum pump housing 308.

The vacuum pump housing 308 contains a vacuum pump (not shown) and defines a space or housing 310 for one or more batteries, preferably configured in a battery pack (not shown). The battery pack provides DC power to a vacuum pump. A potentiometer knob 312 is positioned on an outside surface of the vacuum pump housing 308 and is used to operate a potentiometer (not shown) to regulate the DC voltage applied from the battery pack to the vacuum pump.

A collection reservoir 314 is positioned below and connected to the vacuum chamber 302. The collection reservoir 314 collects liquids, such as, for example, blood or lymph, vented through the patient's chest tube 106 into the vacuum chamber 302.

Generally, a vacuum created by the vacuum pump in the vacuum pump housing 308 creates a low pressure condition inside the vacuum chamber 302. When there is gas or liquid in a surgical site within the patient's body at a pressure greater than the pressure in the vacuum chamber 302, that gas or liquid migrates through the chest tube 106, through the drainage tube port 108, and into the vacuum chamber 302. Any liquid entering the vacuum chamber 302 drains into the collection reservoir 314 or collects on a series of baffles 304 and eventually drains into the collection reservoir 314. Gas entering the vacuum chamber 302 flows around the baffles 304, through the flow meter 306, and into the atmosphere via the vacuum pump (not shown). The amount of vacuum created in the vacuum chamber 302 is controlled by the potentiometer knob 312. By rotating the potentiometer knob 312, the amount of vacuum created by the vacuum pump is changed, thereby changing the suction force present at the end of the chest tube 106 within the patient's body. The amount of air flow through the chest tube 106 is indicated by the flow meter 306 which, in turn, is used to adjust the potentiometer. Generally, if the air flow is high, the voltage is increased. As the air flow decreases, the voltage may be reduced.

The present invention may be used by connecting the drainage tube port to a chest drainage tube following surgery while a patient is still under general anesthesia. At that time, the chest tube drainage system may be turned on by rotating the potentiometer switch. The practitioner may adjust the potentiometer until flow characteristics indicated by the flow meter correspond favorably to an amount of air leak which may persist for some time at a lung. Following the effects of anesthesia, the practitioner may advantageously initiate early ambulatory therapy wherein the patient walks with the portable chest tube drainage system actively venting the surgical site.

The vacuum pump housing 308 will now be described with reference to FIGS. 4A–4E. The vacuum pump housing 308 defines generally a parallelepiped-shaped volume having six rectangular sides. Walls of the vacuum pump housing 308 are preferably made from a substantially rigid, lightweight material, such as plastic, and have a thickness of approximately 0.05 inches. It will be appreciated that the present invention will work with vacuum pump housings of different shapes and/or made from plastic or other materials of varying thicknesses.

A circular inlet 402 interrupts and is formed into a top wall 403 of the vacuum pump housing 308. A gasket 404 sealingly engages the edges of the circular inlet 402. The circular inlet 402 and the gasket 404 provide a connection from the vacuum pump housing 308 to the vacuum chamber 302.

A battery pack housing 310 is advantageously defined within the vacuum pump housing 308. The battery pack housing 310 is partially defined by a front wall 406 of the vacuum pump housing 308 and is accessible through a rectangular interruption formed into the top wall 403. Three additional side walls depending downward from the edges of the rectangular interruption and perpendicular to the top wall 403 along with a lower wall 405 providing a floor, define a parallelepiped-shaped volume of the battery pack housing 310. The lower wall 405 joins the three additional walls substantially at their lower-most edges, and is attached to the front wall 406 in a manner perpendicular thereto. The three additional walls and lower wall defining the battery pack housing 310 are preferably formed from the same material as the walls of the vacuum pump housing 308. The attachments of the walls are accomplished either by integral formation, or by solder or weld points, or by cement or epoxy, or by other attachment mechanisms, as is appropriate for the material of the walls.

The battery pack housing 310, in a preferred embodiment, is of sufficient size to contain an arrangement of ten (10) double-A (AA) sized batteries. It will be appreciated that the present invention will work with different configurations of batteries and with battery pack housings of different sizes, shapes, or materials, and the present invention is not limited to a battery pack housing formed into the vacuum pump housing 308. Nor is the present invention limited by the number, type or voltage of batteries, as those of ordinary skill will appreciate that differing configurations may operate with differing power source characteristics.

A shaft inlet 408 and a vent hole 409 interrupt and are formed into the front wall 406 below the battery pack housing 310 and above a junction of the front wall 406 and a lower wall 412 of the vacuum pump housing 308. The shaft inlet 408 permits a potentiometer shaft (not shown) to extend through the front wall 406 to connect the potentiometer knob 312 (FIG. 3) on the outer side of the front wall 406 to a potentiometer (not shown) within the vacuum pump housing 308. The vent hole 409 positioned above the shaft inlet 408 permits gases exhausted by the vacuum pump to exit the vacuum pump housing 308 into the atmosphere.

The vacuum pump housing 308 further defines a vacuum pump space 410 within the vacuum pump housing 308. The vacuum pump space 410 may be of any size and shape which accommodates a sufficient vacuum pump (not shown). In a preferred embodiment, however, the vacuum pump space 410 is approximately a three-dimensional L-shaped volume formed about the battery pack housing 310.

A collection reservoir attachment slot 414 (FIG. 4E) runs partially around the perimeter of the bottom of the vacuum pump housing 308. In a preferred embodiment, the collection reservoir attachment slot 414 is formed along the bottom edges of the front wall 406 and the adjoining side walls. The bottom edges of those three walls extend approximately one-quarter of an inch (¼") below the floor 412 of the vacuum pump housing 308. The slot 414 is defined by three short walls 416, 418, 420 extending vertically from the floor 412 to the respective bottom edges of the front wall 406 and the adjoining side walls of the vacuum pump housing. The three short walls 416, 418, 420 are positioned parallel to respective bottom portions of the front wall 406 and the adjoining side walls, approximately one sixteenth of an inch (¹⁄₁₆") away from those walls. The collection reservoir attachment slot 414 advantageously receives a connecting ridge of a collection reservoir to permit simple manual connection and removal of a collection reservoir.

Further details of the vacuum pump housing 308 will now be described with reference to FIGS. 5A–5D. A vacuum pump 502 is contained within the vacuum pump space 410. The vacuum pump 502 is secured to the lower wall 412 of the vacuum pump housing 308. In one embodiment, the vacuum pump 502 is manufactured by Nitto Kohki Co., Ltd., of Tokyo, Japan under the model designation DPO 140-X1-0001. The vacuum pump 502 may be operated by supplying it with a voltage ranging from about three (3) to about twelve (12) volts DC.

In one embodiment, the vacuum pump 502 generates a distinct vacuum power for each supplied voltage. A correlation between supplied voltage and vacuum power advantageously permits regulating the suction force of the chest tube drainage system 102.

For example, the vacuum pump 502 generates about 0.9 liters per minute of air flow at a zero inflow resistance when supplied with three (3) volts DC power, and generates about 3.9 liters per minute of air flow at a zero inflow resistance when supplied with twelve (12) volts DC power. It will be appreciated that this maximal air flow, 3.9 liters per minute, is equivalent to around 22% of air leak of one breath of 900 ml at a rate of 20 breaths per minute. For reference purposes, it has been observed that a high minute ventilation such as 18 liters per minute (=900 ml*20 breaths) is generally seen only in a large male patient. If more than around 22% of inhaled air leaks out, it is difficult to maintain adequate ventilation for a patient, and a surgical intervention to close the leak in the lung may become necessary. As will be appreciated, therefore, the power generated by the vacuum pump 502 is sufficient for usual clinical conditions.

High vacuum pressure generated by extremely powerful central vacuum lines of typical hospital facilities generally cause lacerations when applied to lung tissue. In contrast, the vacuum pump 502 generates a suction pressure of approximately −400 torr (−544 cm $H_2O$) at a zero inflow resistance and when supplied with 12 volts. Due to the comparatively small vacuum power of the vacuum pump 502, an inadvertent laceration of the lung generally does not occur even if an inflow port 108 is accidentally shut off, e.g., clogged with blood clots, and lung tissue is sucked against the chest tube. Thus, advantageously, the drainage system of the present invention is safe for use even by inexperienced personnel. Even when the drainage system of the present invention is used with patients having extremely friable lung tissue, such as patients suffering from emphysema, a vacuum relief valve (FIGS. 10A, 10B, 10C) acts as a double safety feature, and can, for example, maintain the vacuum pressure at a lower, even safer threshold.

The vacuum pump 502 may be removably attached to the vacuum pump housing 308. In one embodiment, the vacuum pump 502 is secured by four (4) screws 504 extending through holes in a base portion 506 of the vacuum pump 502 to threadingly engage the lower wall 412 of the vacuum pump housing 308. Of course, other methods of attachment such as nuts arranged outside the lower wall 412 or countersunk into inward cylindrical projections of the lower wall 412 may also be used. Alternatively, the vacuum pump 502 may be fixedly attached to the lower wall 412 of the vacuum pump housing 308, such as, for example, through the use of solder points or welds, or the use of cement or epoxy, as appropriate to form a permanent bond between the respective materials of the vacuum pump 502 and the vacuum pump housing 308.

A vacuum inlet 508 on an upper end 510 of the vacuum pump 502 is connected to an end of vacuum tubing 512. The gasket 404 sealingly engages the outer periphery of the vacuum tubing 512 at the point where it extends through the inlet 402, which in turn connects to the flow meter 306.

A vacuum outlet 514 discharges into the atmosphere gases received through the vacuum inlet 508. The discharged gases flow around the exterior of the vacuum pump 502 and exit the vacuum pump housing 308 through the vent hole 409.

The potentiometer knob 312 connects to the potentiometer shaft 516, which rotates to control a potentiometer 518. The potentiometer 518 may be any of a number of known potentiometers which can regulate a supplied DC voltage of twelve (12) volts to generate a range of voltages from about twelve (12) volts down to about three (3) volts. Optionally, the potentiometer 312 includes an off position, creating a break in supplied voltage, and, in that position, the potentiometer 312 supplies no voltage and the vacuum pump 502 provides no vacuum force.

A potentiometer line 520 connects a first terminal of a motor 522 of the vacuum pump 502 to a first terminal of the potentiometer 518. A first power line 524 connects a second terminal of the potentiometer to a first terminal of a battery pack 526. A second power line 528 connects a second terminal of the battery pack 526 to a second terminal of the motor 522.

The battery pack 526, preferably can provide twelve (12) volts DC continuously over a period of about four hours, and can provide lesser voltages for even longer periods of time. One such battery pack is manufactured by Sanyo of Tokyo, Japan and comprises multiple nickel-cadmium batteries.

The battery pack 526 is removable. As will be appreciated by those of ordinary skill, the battery pack has two accessible terminals (not shown), one positive and one negative. The negative terminal connects negative posts of each of the batteries in the battery pack, and the positive terminal connects the positive posts of each of the batteries. Receiving terminals (not shown) within the battery pack housing 310 are configured and arranged to touchingly engage the accessible terminals of the battery pack 526 when the battery pack 526 is installed.

When the power of a battery pack 526 is substantially exhausted, it may be removed and another charged battery pack 526 may be installed in its place. Optionally, the present invention may have an internal recharging system (not shown). The recharging system includes a removable AC power cord (not shown). One end of the AC power cord may be connected to a jack (not shown) on the outside of the vacuum pump housing 308, the jack directing power to the internal recharging system, and another end of the AC power cord may be plugged into a standard electrical outlet, such as one supplying 110 volts AC. As will be appreciated by those of ordinary skill, the internal recharging system transforms the 110 volts AC supplied through the AC power cord, into voltage appropriate to recharge the nickel-cadmium batteries of a battery pack 526 installed in the battery pack housing 310. While the battery pack 526 is recharging, the internal recharging system routes twelve (12) volts DC power to the receiving terminals in the battery pack housing 310. In this manner, power may be supplied to the vacuum pump 502, and the chest tube drainage system 102 may be operated while an installed but exhausted battery pack 526 recharges. In a further embodiment, the chest tube drainage system 102 may be operated with no battery pack 526 installed in the battery pack housing 310, but with the AC power cord connected to the jack and plugged into an electrical outlet, the internal recharging system supplying approximately twelve (12) volts DC to the receiving terminals in the battery pack housing 310. It will be appreciated that this mode of operation can be alternatively accomplished by an appropriate AC to DC converter.

The vacuum chamber 302 and the flow meter housing 626 will now be described in detail with reference to FIGS. 6A–6C. The vacuum chamber 302 comprises a top wall 602, a bottom wall 604, a front wall 606, a rear wall 608, and side walls 610, 612. Those walls define the parallelepiped-shaped outer shell of the vacuum chamber 302.

The drainage tube port 108 extends through a circular interruption in the top wall 602. The drainage tube port 108 is approximately cylindrical in shape, with a central bore in fluid contact with a space defined within the vacuum chamber 302. The chest tube 106 seals around the outer surface of the cylindrical wall of the drainage tube port 108.

A curved drain wall 614 is positioned within the parallelepiped-shaped volume defined by the outer shell of the vacuum chamber 302. A top edge 616 of the drain wall 614 blends into the inner surface of the front wall 606 at a point approximately midway between the upper and lower edges of the front wall 606. Curved side edges of the drain wall 614 blend into inner surfaces of the side walls 610, 612 of the vacuum chamber 302. A lower edge 618 of the drain wall 614 connects to the bottom wall 604 of the vacuum chamber 302, such that the lower edge 618 of the drain wall 614 is parallel to respective bottom edges of the front wall 606 and the rear wall 608 of the vacuum chamber 302. The lower edge 618 of the drain wall 614 preferably attaches to the lower wall 604 of the vacuum chamber 302 at a point closer to the rear wall 608 than to the front wall 606.

A first baffle 620, a second baffle 622, and a third baffle 624 define planar surfaces approximately parallel to planar surfaces defined by the front wall 606 and the rear wall 608 of the vacuum chamber 302. A top edge of the baffle 620 is attached to the inner surface of the top wall 602 of the vacuum chamber 302. That attachment occurs preferably at a point closer to the rear wall 608 than to the front wall 606. The circular interruption in the top wall 602 for the drainage tube port 108 is formed into the top wall 602 at a position between the rear wall 608 and the first baffle 620.

Side edges of the first baffle 620 are attached to the side walls 610, 612. A bottom edge of the first baffle 620 extends preferably to a point just above, but not touching, the bottom wall 604 of the vacuum chamber 302.

Side edges of the second baffle 622 are attached to side walls 610, 612. A top edge of the second baffle 622 is preferably positioned just below, but not touching the inner surface of the top wall 602. A bottom edge of the second baffle 622 is preferably positioned just above, but not touching, the surface of the drain wall 614.

Side edges of the third baffle 624 are attached to the side walls 610, 612 of the vacuum chamber 302. A top edge of the third baffle 624 is preferably positioned below, but not touching, the inner surface of the top wall 602 of the vacuum chamber 302. A bottom edge of the third baffle 624 is preferably positioned just above, but not touching, the drain wall 614.

The third baffle 624 defines a planar surface positioned approximately equidistant between planar surfaces defined by the front wall 606 and the second baffle 622. The second baffle 622 defines a planar surface positioned approximately equidistant between the planar surfaces defined by the third baffle 624 and the first baffle 620. The first baffle 620 defines a planar surface positioned approximately equidistant between planar surfaces defined by the second baffle 622 and the rear wall 608 of the vacuum chamber 302.

In one embodiment of the present invention, the side walls 610, 612 extend vertically below the bottom wall 604 approximately one-quarter of an inch (¼") to define collection reservoir attachment slots. Short walls 615, 617 extend downward from the bottom wall 604 to the respective bottom edges of the side walls 610, 612. The short walls 615, 617 are parallel to the respective side walls 610, 612 and are spaced approximately one-sixteenth of an inch (¹⁄₁₆") therefrom to define the collection reservoir attachment slots 611, 613. The collection reservoir attachment slots advantageously receive an attachment ridge of a collection reservoir 314 to permit easy and convenient manual attachment of same to the vacuum chamber 302.

Other means may be used to attach a collection reservoir to the vacuum chamber 302, such as, for example, opposing hook and loop structures (e.g., Velcro®) respectively located on the outer surface of the bottom 604 of the vacuum chamber 302 and the top surface of the collection reservoir 314 such that, when the collection reservoir is in operable relation with the vacuum chamber 302, the two hook and loop structures touchingly engage each other until a separating force disengages them.

The flow meter housing 626 is mounted on the vacuum chamber 302. In one embodiment of the present invention, a top wall 628 of the flow meter housing 626 extends from the planar surface of the top wall 602 of the vacuum chamber housing 302 in a direction toward the front wall 606 of the vacuum chamber housing 302. A bottom wall 630 of the flow meter housing 626 defines a planar surface parallel to and coextensive with the top wall 628 of the flow meter housing 626. Side walls 632, 634 define planar surfaces parallel with and extending from the respective planar surfaces defined by the side walls 610, 612 of the vacuum chamber 302. Top and bottom edges of the side walls 632, 634 attach to respective top and bottom edges of the top wall 628 and bottom wall 630 of the flow meter housing.

A front wall 636 of the flow meter housing 626 attaches from a front edge of the top wall 628 to a front edge of the bottom wall 630. Side edges of the front wall 636 connect to front edges of the side walls 632, 634. Rear edges of the top wall 628, the bottom wall 630, and the side walls 632, 634 connect to an upper portion of the front wall 606 of the vacuum chamber 302. That upper portion defines a planar surface coextensive with and parallel to the planar surface defined by the front wall 636 of the flow meter housing 626. The upper portion of the front wall 606, the top wall 628, the bottom wall 630, the side walls 632, 634, and the front wall 636 define a parallelepiped-shaped volume which contains the flow meter 306.

The front wall 636 is advantageously at least partially transparent to permit the viewing of the flow meter therethrough. Also, the front wall 636 is interrupted by a circular hole about which is positioned, preferably on the inner surface of the front wall 636, a vacuum relief valve 637.

Figure 10A:
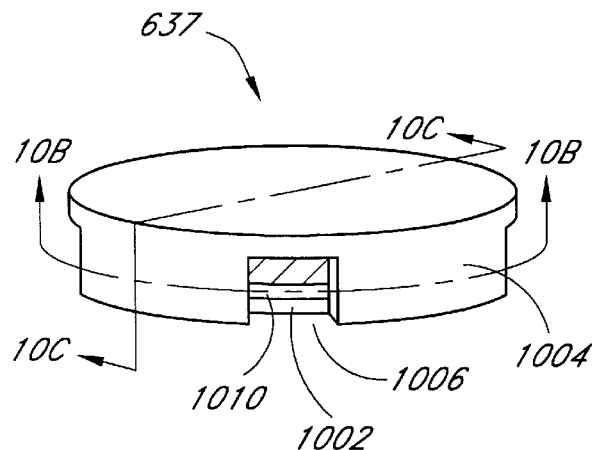
FIG. 10A illustrates a perspective representation of a vacuum relief valve in accordance with one embodiment of the present invention.
Figure 10B:
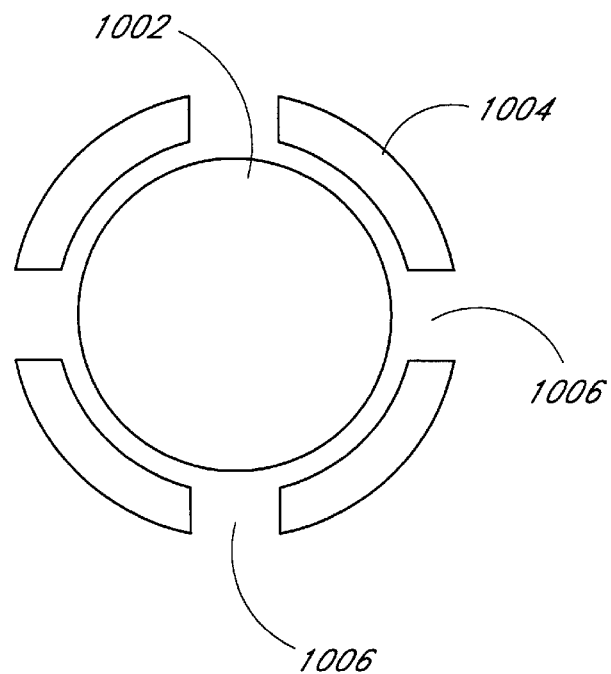
FIG. 10B illustrates a bottom view of a cross-section of a vacuum relief valve in accordance with one embodiment of the present invention.
Figure 10C:
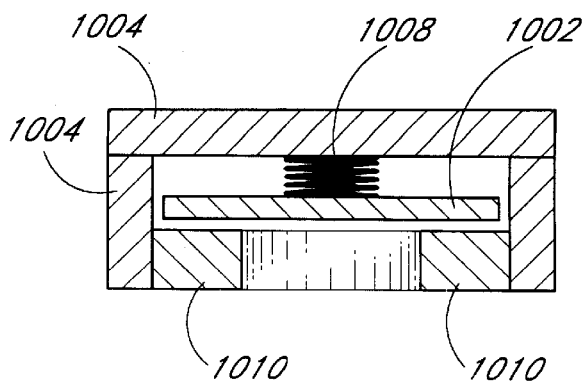
FIG. 10C illustrates a side view of a cross-section of a vacuum relief valve in accordance with one embodiment of the present invention.

The vacuum relief valve 637, shown in detail in FIGS. 10A–10C, includes a vacuum relief valve housing 1004 with a vacuum relief disc 1002 disposed therein. A cylindrical sidewall of the vacuum relief valve housing 1004 is interrupted by at least one, and preferably four, vacuum relief slots 1006 providing fluid communication between the space defined by the vacuum relief valve housing 1004 and the space defined by the flow meter housing 626. A vacuum maintenance spring 1008 connects the vacuum relief disc 1002 to the inside of the circular top surface of the vacuum relief valve housing 1004. Also disposed inside the vacuum relief valve housing is a vacuum seal ring 1010. The vacuum seal ring 1010 is sealingly attached around the circumference of the hole in the front wall 636 (FIG. 6). The vacuum seal ring 1010 has an outer diameter slightly smaller than the inner diameter of the vacuum relief valve housing 1004, and it has an inner diameter smaller than the outer diameter of the vacuum relief disc 1002.

The vacuum maintenance spring 1008 is configured to exert a force upon the vacuum relief disk 1002 to push it against the top surface of the vacuum seal ring 1010. The force exerted by the vacuum relief spring 1008 upon the vacuum relief disc 1002 is sufficient to cause the vacuum relief disc 1002 to sealingly engage the vacuum seal ring 1010, thereby maintaining a vacuum in the flow meter housing 626 and, likewise, the vacuum chamber 302. When vacuum pressure inside the flow meter housing 626 reaches a predetermined level, the vacuum maintenance spring 1008 compresses. The predetermined level is set at a level just below the level where the vacuum force may damage bodily tissue when presented proximate to such tissue through an end of a chest tube. When the predetermined vacuum level is reached, the vacuum maintenance spring 1008 compresses, causing the vacuum relief disc 1002 to separate from the vacuum seal ring 1010. That separation creates a vacuum leak allowing air outside the flow meter housing 626 to enter the flow meter housing 626 via one or more of the vacuum relief slots 1006, which, in turn, results in a decrease of the vacuum force to a safe level. When the vacuum decreases to an amount insufficient to compress the vacuum maintenance spring 1008, the vacuum relief disc 1002 again seals around the vacuum seal ring 1010. Thus, the vacuum is advantageously maintained at an operable, but non-injurious level.

The flow meter 306 will now be described in detail with reference to FIGS. 7A–7E. The flow meter 306 is positioned within the flow meter housing 626, preferably adjacent to either side wall 632 or 634 of the flow meter housing 626. The flow meter 306 includes a flow meter tube 702, which defines a cylindrical inner space within which a floating ball 704 rests. The floating ball 704 moves freely within the flow meter tube 702, but retaining members 716 (FIG. 7E) located inside the flow meter tube 702 at the openings at each end prevent the floating ball 704 from escaping the flow meter tube 702. At all places along the length of the flow meter tube 702, the inner diameter of the flow meter tube 702 is greater than the diameter of the floating ball 704. Thus, the floating ball 704 may move freely within the flow meter tube 702, and gas, such as ambient air, may flow between the flow meter tube 702 and the floating ball 704. The diameter of the floating ball 704, the weight of the floating ball 704, and the inner diameter of the flow meter tube 702 are all compatibly configured such that the floating ball 704 rests substantially near the bottom of the flow meter tube 704 when there is little or no leak from a patient's lung(s), and such that the floating ball 704 rests substantially near the top of the flow meter tube 704 when a substantial leak exists in a patient's lung(s).

The flow meter 306 includes a 3-dimensional L-shaped structure 706 that defines a 3-dimensional, L-shaped air conduit. The L-shaped structure 706 comprises a vertical portion 708 and a horizontal portion 710. An intake port 712 is formed within a back wall of the vertical portion 708. The intake port 712 is in fluid contact with the 3-dimensional, L-shaped air conduit within the structure 706.

A circular inlet hole 714 is formed within an upper surface of the horizontal portion 710 of the flow meter 306. A bottom end of the flow meter tube 702 is attached around the edges of the circular inlet hole 714. Thus, the inner space of the flow meter tube 702 is in fluid contact with the 3-dimensional, L-shaped air conduit and the intake port 712, which, in turn, is in fluid contact with the space inside the vacuum chamber 302.

A bottom surface of the horizontal portion 710 of the flow meter 306 is attached to the bottom wall 630 of the flow meter housing 626. A rear wall of the vertical portion 708 of the flow meter 306 is attached to an upper portion of the front wall 606 of the vacuum chamber 302, such that an intake port 638 (FIG. 6B) formed into one side of the front wall 606, is in fluid contact with the intake port 712.

A vacuum outlet tube 640 (FIGS. 6A, 7B, 7D) is attached to the bottom wall 630 of the flow meter housing 626 about a hole 641 formed proximate to the center of the surface area defined by the bottom wall 630. The end of the vacuum outlet tube 640 furthest from the flow meter housing 626 fits sealingly within the tubing 512 (FIG. 5C), and the vacuum outlet tube engages the inner edges of the gasket 404 (FIG. 4B) when positioned through the hole 402 to bring the flow meter and the vacuum chamber 302 into operable relation with the vacuum pump housing 308. The vacuum outlet tube 640 defines a cylindrical space which is in fluid contact with the space within the flow meter housing 626, which, in turn, is in fluid contact with the cylindrical space within the flow meter tube 702. A one-way umbrella valve 642 is positioned within the vacuum outlet tube 640.

Figure 9A:
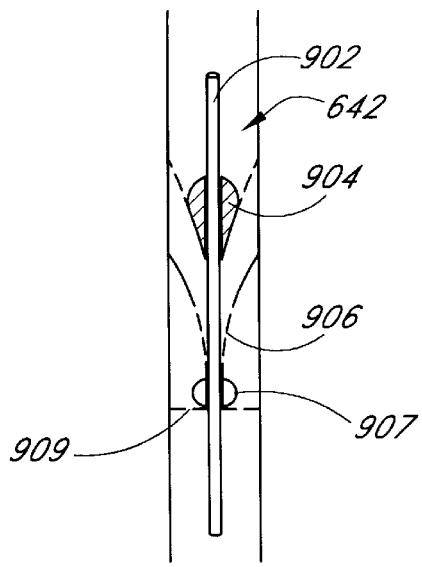
FIG. 9A illustrates a side view cross-section of a one-way umbrella valve in accordance with an embodiment of the present invention.
Figure 9B:
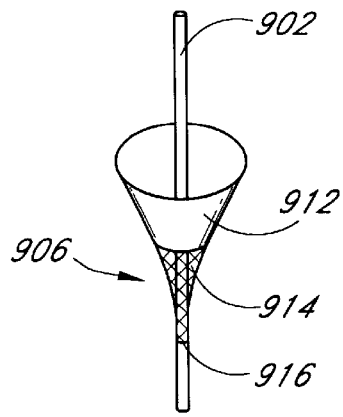
FIG. 9B illustrates a representation of a floating occluder portion of a one-way umbrella valve in accordance with an embodiment of the present invention.
Figure 9C:
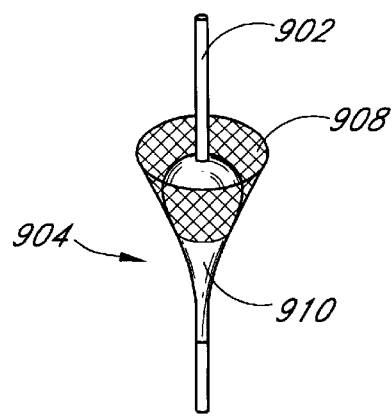
FIG. 9C illustrates a representation of a stopper portion of a one-way umbrella valve in accordance with an embodiment of the present invention.

The one-way umbrella valve 642 is shown in detail in FIGS. 9A–9C. The one-way umbrella valve 642 includes a shaft 902, a stopper portion 904 and a floating occluder portion 906. The stopper portion 904 is shaped approximately like an upside-down cone and comprises, at the base end, an upper mesh 908, porous to gas and liquid, and, at the tip end, a lower, non-porous stop 910. The upper mesh 908 is secured to the walls of the cylindrical tube in which the one-way umbrella valve 642 is situated, and, thus, in this embodiment, the stopper portion 904 is fixed relative to the cylindrical tube. At a point located a distance of approximately one-half the height of the stopper portion 904 cone, travelling upward from its tip, the upper mesh 908 is joined to the non-porous stop 910 around its circumference. A travel hole 916 having a diameter slightly larger than the diameter of the shaft 902 runs through the stopper portion 904 from top to bottom permitting the shaft 902 to slide therethrough.

The floating occluder portion 906 is also shaped approximately like an upside-down cone and configured such that its inner surface fits closely to the outer surface of the stopper portion 904. The floating occluder portion 906, comprises, at the base end, an upper, non-porous stop band 912, and, at the tip end, a lower mesh 914, which is porous to gas and liquid. At a point located a distance of approximately one-half the height of the floating occluder portion 904 cone, and travelling upward from its tip, the non-porous stop band 912 is joined to the lower mesh 914 around its circumference.

At the tip end of the floating occluder portion 906, the lower mesh 914 is connected to an approximately spherical stopper ball 907 which is configured about and fixed to the shaft 902. Thus, the stopper ball 907, the shaft 902, and the floating occluder portion 906 may travel together. Because the diameter of the stopper ball 907 is substantially less than that of the circular tube, liquids and gases pass freely by the stopper ball 907.

Positioning spokes 909 are fixed to and radiate inward from the walls of the cylindrical tube to a ring section in the middle of the spokes 909. A hole in the ring section having a diameter slightly larger than the diameter of the shaft 902 permits the shaft 902 to slide therethrough. In combination with the travel hole 916, the hole in the ring section holds the shaft 902 and the floating occluder portion 906 in a position parallel to and in the center of a cylindrical tube, such as the vacuum outlet tube 640 or the drain tube 644.

In one embodiment, six positioning spokes 909 are equally spaced around a circular section of the cylindrical tube to create 60 degree angles between any adjoining pair. The length of each positioning spoke 909 is slightly shorter than the distance between the shaft 902 and the wall of a tube in which the umbrella valve 642 is placed. Because each of the positioning spokes 909 is made of a thin, rigid material, such as plastic rod or metal wire, gases and liquids flowing in the tube pass freely by the positioning spokes 909.

The floating occluder portion 906 is positioned in the cylindrical tube between the upper stopper 904 and the positioning spokes 909. One end of the shaft 902 is inserted through the travel hole 916 in the upper stopper 904, and the other end of the shaft 902 is inserted through the ring section in the center of the positioning spokes 909. The stopper ball 907 has a diameter larger than the ring section in the center of the positioning spokes 909 and thus the stopper ball 907 prevents movement of the floating occluder portion 906 to a point beyond the positioning spokes 909.

When the floating occluder portion 906 occupies a position along the shaft 902 spaced apart from the stopper portion 904, liquid or gas may flow past the stopper portion 904 and the floating occluder portion 906. However, when the floating occluder portion 906 moves toward and rests up against the stopper portion 904, the stop band 912 of the floating occluder 906 substantially prevents liquids or gas from flowing through the upper mesh 908 of the stopper portion 904, and the non-porous stop 910 of the stopper portion 904 substantially prevents liquids or gas from flowing through the lower mesh 914 of the floating occluder 906. In that manner, the one-way umbrella valve permits gas or liquid to flow in a direction from the stopper portion 904 and toward the floating occluder 906, but substantially prevents gas or liquid from flowing in the opposite direction.

It will be appreciated that other types of one-way valves may be used with the present invention, and that the present invention is not limited by a particular type of one-way valve.

Referring back to FIGS. 6A, 6B and 6C, a drain tube 644 extends from a hole 646 formed in the bottom wall 604. The drain tube 644 is positioned proximate the bottom wall 604 between the drain wall 614 and the rear wall 608. The drain tube 644 defines an inner cylindrical space in fluid contact with the space defined by and within the vacuum chamber 302. A one-way umbrella valve 646 is positioned within the drain tube 644. The one-way umbrella valve 646 is configured as described in relation to FIGS. 9A, 9B and 9C.

Figure 8A:
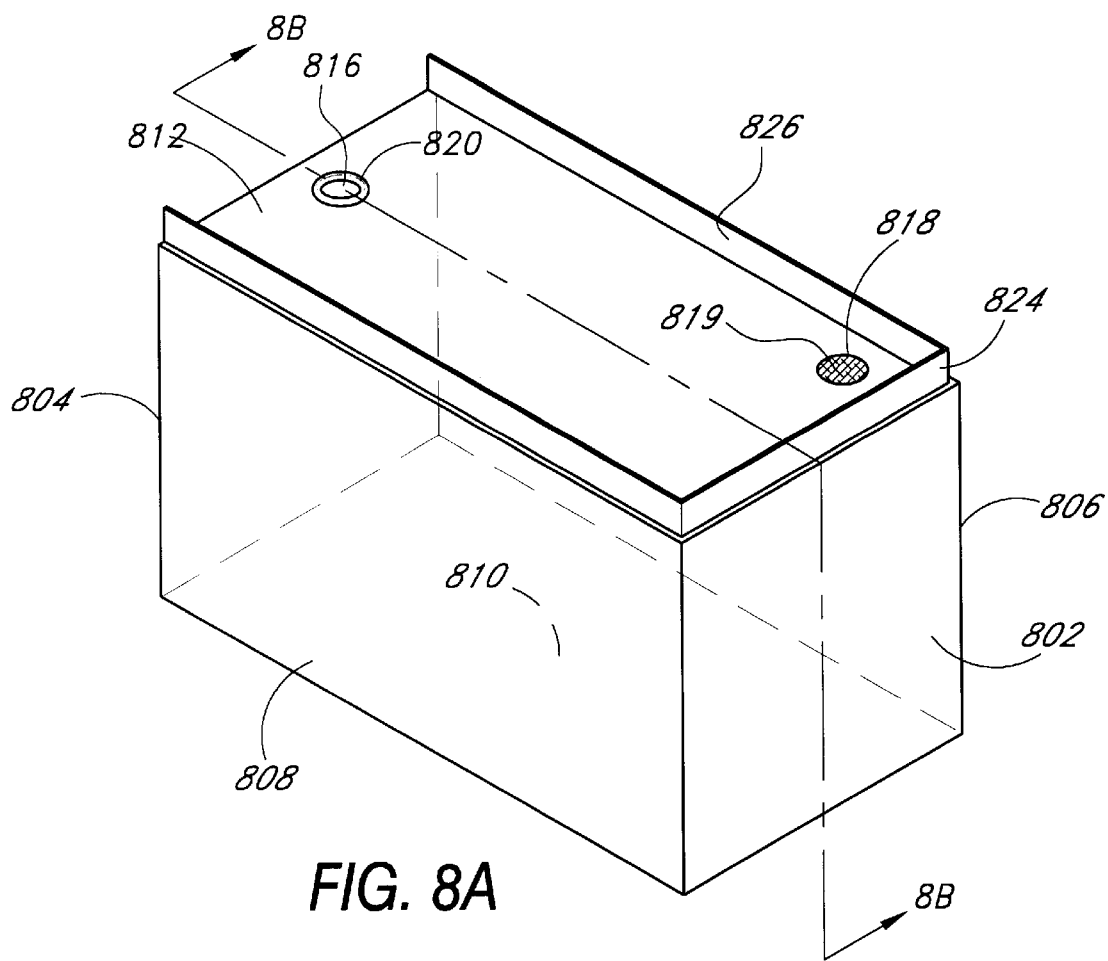
FIG. 8A represents an illustration of a collection reservoir in accordance with an embodiment of the present invention.
Figure 8B:
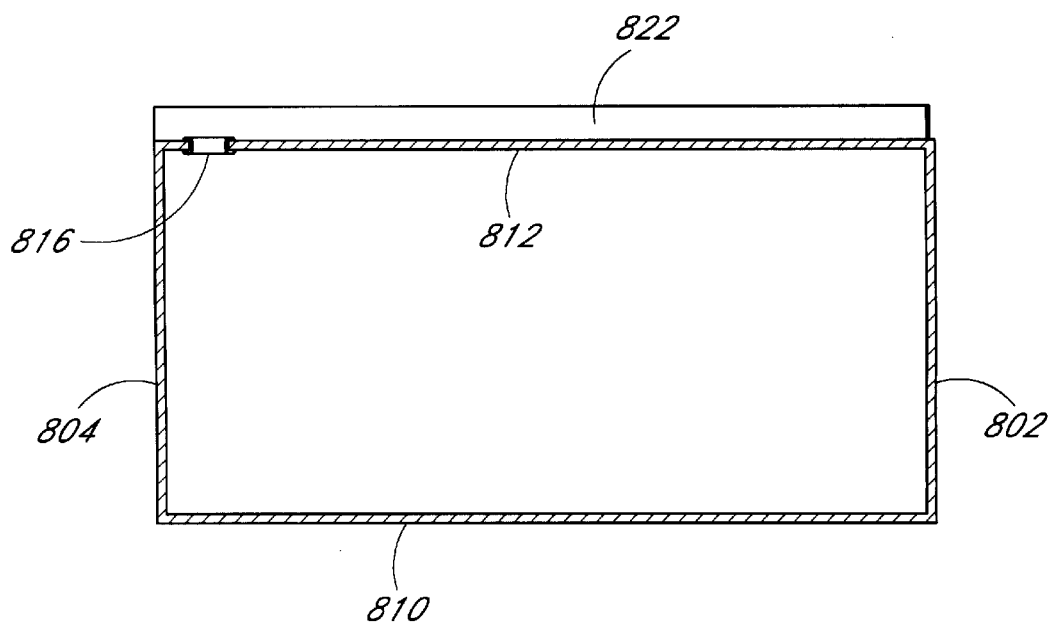
FIG. 8B represents a cross-sectional view of a collection reservoir in accordance with an embodiment of the present invention.

The collection reservoir 314 will now be described with reference to FIGS. 8A–8C. The collection reservoir 314 generally defines a parallelepiped-shaped space, having four sidewalls—a front sidewall 802, a back sidewall 804, a right sidewall 806 and a left sidewall 808—and a top surface 812 and a bottom surface 810. A circular hole within the top surface 812 defines an input port 816. A sealing gasket 820 surrounds the perimeter of the input port 816 to sealingly engage the outer surface of the drain tube 644 (FIG. 6B). A second circular hole interrupts the top surface 812 to define an exhaust port 818, across which, preferably, is stretched a gas-permeable material 819, such as gortex.

Three short walls projecting upward from the collection reservoir 314 form an approximately u-shaped connecting ridge, which is received by corresponding attachment slots along the respective bottoms of the vacuum chamber 302 and the vacuum pump housing 308. The first short wall 822 runs parallel to and along the upper edge of the left sidewall 808, offset inwardly approximately 0.05 inches. Like the second and third short walls, the first short wall 822 is about ¼" high and 0.05 inches thick. The second short wall 824 runs parallel to and along the upper edge of the front wall 802, and the third short wall 826 runs parallel to and along the upper edge of the right sidewall 806. The second 824 and third 826 short walls are offset 0.05 inches inwardly.

To attach the collection reservoir 314, an operator fits the drain tube 644 into the input port and fits the unshaped connection ridge into the receiving attachment slots on the vacuum chamber 302 and the vacuum pump housing 308. The u-shaped connection ridge advantageously permits the collection reservoir 314 to be connected to the combined vacuum chamber 302 and vacuum pump housing 308 components with simple manual force. As indicated above, in an alternative embodiment, hook and loop structures (e.g., Velcro®) could replace the u-shaped connection ridge and receiving attachment slots to permit the collection reservoir 314 to be attached. It will thus be appreciated by those of ordinary skill that the present invention is not limited by any technique for attaching the collection reservoir 314.

Figure 11:
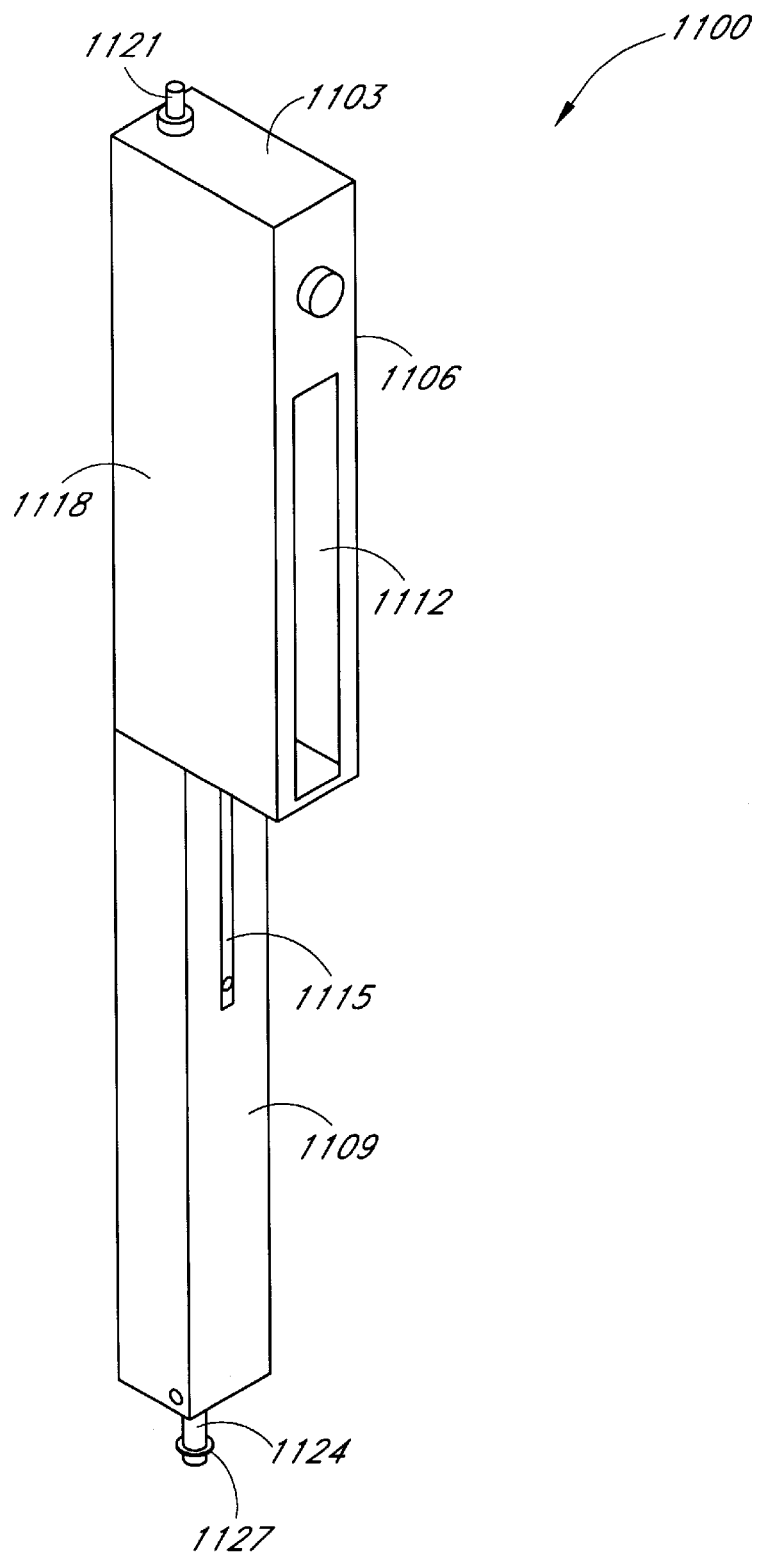
FIG. 11 illustrates a perspective view of a miniature chest tube drainage system in accordance with an alternative embodiment of the present invention.

FIG. 11 represents an illustration of an alternative embodiment of the present invention. Advantageously, the embodiment represented in FIG. 11 is lighter and more compact, while still providing effective chest tube drainage. The chest tube drainage system of FIG. 11 is a single-unit, self-contained drainage system 1100 combining the three main parts of the previously described system; a housing for vacuum pump 1103, a battery pack container 1112, and a vacuum chamber 1118. The self-contained drainage system 1100 measures approximately 5 cm by approximately 40 cm. The drainage system 1100 includes a main chamber 1106 that includes the vacuum pump housing 1103, the battery pack container 1112, and a top portion of the vacuum chamber 1118. A lower portion 1109 of the vacuum chamber 1118 extends below the main chamber 1106.

The vacuum chamber 1118 contains one or more baffles (not shown) extending vertically for nearly the length of vacuum chamber 1118. The baffles operate to separate liquid and gases from vented fluids. In one embodiment, a baffle connected to parallel sides of the vacuum chambers extends from its connection at and to the bottom of the lower portion of the vacuum chamber 1109 up to a point just below but not touching the inside of the top surface of the vacuum chamber 1118. Also, a vacuum relief valve (not shown) such as that discussed in connection with FIG. 10 is located preferably on the lower portion of the vacuum chamber.

As fluid is vented, the air in the vented fluid is exhausted from the vacuum chamber 1118 through one or more exhaust holes (not shown) formed in either the main chamber 1106 or the lower vacuum chamber 1109. The liquid in the vented fluid drains from the baffles to the bottom of the lower vacuum chamber 1109 and exits the drainage system 1100 through a drainage port 1124. As is known in the art, a leg bag (not shown) may be used to collect the vented liquid from the drainage port 1124. Drainage tubing (not shown) fits snuggly on the drainage port 1124, and a seal is formed with the drainage tubing by a sealing ring 1127. The drainage tubing connects the drainage port 1124 to the leg bag.

The vacuum pump housing 1103 of the self-contained drainage system 1100 is smaller in size that the vacuum pump housing 308 of the drainage system 102, and advantageously uses a smaller and lighter vacuum pump. The self-contained drainage system 1100 uses a DC powered miniature vacuum pump to provide the suction power. One such miniature vacuum pump is the Sensidyne AA series of pumps, measuring less than 1.6 cubic inches in total size. The AA pumps provide flow rates up to 2.7 liters per minute with a maximum pressure of 9 psig and a vacuum of 16" Hg. Optionally, a potentiometer regulates vacuum generated by the vacuum pump and provides on/off control as discussed in connection with FIG. 5A.

A flow meter 1115 is integrated within the lower vacuum chamber 1109 to indicate the amount of air flow. In the context of a patient recovering from lung-related surgery, the flow meter 1115 indicates an amount of air leak from the patient's lung(s). The amount of air flow through the chest tube is indicated by the flow meter 1115 which, in turn, is used to adjust the amount of vacuum provided by the vacuum pump.

Generally, a vacuum created by the vacuum pump in the vacuum pump housing 1103 creates a low pressure condition inside the vacuum chamber 1118. When there is gas or liquid in a surgical site within the patient's body at a pressure greater than the pressure in the vacuum chamber 1118, that gas or liquid migrates through a chest tube, through the drainage tube port 1121, and into the vacuum chamber 1118. Any liquid entering the vacuum chamber 1118 drains immediately through the drainage port 1124 into a leg bag (or other appropriate collection device) due to the force of gravity or collects on one or more baffles and eventually drains into the leg bag. Gas entering the vacuum chamber 1118 flows around the baffles, through the flow meter 1115, and into the atmosphere via the exhaust hole.

In one embodiment, the drainage tube port connects to a direction tube (not shown) which extends from the top of the vacuum chamber whereat it connects with the drainage tube port down to a point approximately ½" above the drainage port 1124. The distance from the bottom of the direction tube to the drainage port may vary from embodiment to embodiment. The direction tube advantageously guides vented fluids to a point close to the drainage port 1124 wherein vented liquids may drain.

In each of the embodiments described, vented liquids flow into a collection device under the force of gravity. Because of this, the drainage systems need to be in a generally upright configuration to function properly. To prevent malfunctions, the drainage systems may be equipped with a tilt alarm to indicate the system is not in a proper upright position. The tilt alarm may provide an audible warning, a visual warning, or a combination of the audible and visual warning. The tilt alarm can be comprised of a tilt switch or tiltdetection device known in the art to indicate tilting movement, such as a mercury switch or the like. When the tilt switch detects a tilt condition, it generates a signal, in one embodiment using voltage from the battery pack, which is transmitted to an alarm circuit, the alarm circuit receiving the signal and responsively generating sound (preferably a high-pitched, intermittent sound), or light (preferably a bright, flashing light), or both.

Numerous variations and modifications of the invention will become readily apparent to those skilled in the art. Accordingly, the invention may be embodied in other specific forms without departing from its spirit or essential characteristics. The detailed embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A portable active drainage system, comprising a vacuum source creating a vacuum;

a vacuum chamber having a drainage tube port, a vacuum port and a reservoir port, the vacuum chamber connected to the vacuum source through the vacuum port to apply the vacuum to vent fluid from an animal through the drainage tube port when the drainage tube port is connected to a drainage tube extending from a location inside the animal; and a reservoir having an input port connected to the reservoir port, the reservoir receiving vented liquid through the input port, the reservoir configured in combination with the vacuum source and the vacuum chamber to provide a self-contained and transportable unit.

2. The portable active drainage system as described in claim 1, wherein the vacuum chamber separates gas and liquid from the vented fluid.

3. The portable active drainage system as described in claim 1, further comprising:

a flow meter indicating a flow quantity.

4. The portable active drainage system as described in claim 3, wherein the flow quantity corresponds to a leak in at least one lung of the animal.

5. The portable active drainage system as described in claim 1, wherein the vacuum source includes a vacuum pump and a power source.

6. The portable active drainage system as described in claim 5, wherein the vacuum source is substantially enclosed within a vacuum pump housing.

7. The portable active drainage system as described in claim 6, wherein the power source includes at least one battery and wherein the vacuum pump operates from electrical current provided by the at least one battery.

8. The portable active drainage system as described in claim 7, wherein the battery is a rechargeable battery, and wherein the power source includes a battery recharger configured to charge the battery and provide current suitable to power the vacuum pump.

9. The portable active drainage system as described in claim 6, wherein the power source includes a power converter converting current from a standard electrical outlet to an electrical current suitable to power said vacuum pump and wherein the power converter is configured to be connected to a standard electrical outlet.

10. The portable active drainage system as described in claim 6, further comprising:

a regulating control that regulates the vacuum.

11. The portable active drainage system as described in claim 10, wherein a maximum vacuum permitted by the regulating control is insufficient to injure living tissues exposed to the maximum vacuum.

12. The portable active drainage system as described in claim 6, further comprising:

a vacuum relief valve regulating the vacuum.

13. The portable active drainage system as described in claim 6, further comprising:

a tilt switch detecting tilt along at least one axis and providing a tilt signal when the amount of tilt exceeds a predetermined threshold.

14. The portable active drainage system as described in claim 13, further comprising:

a tilt alarm responding to said tilt signal by generating an audible sound.

15. The portable active drainage system as described in claim 13, further comprising:

a tilt alarm responding to the tilt signal by generating a visible indication of a tilt condition.

16. The portable active drainage system as described in claim 1, wherein the vacuum chamber includes at least one baffle separating liquid and gas from the vented fluid.

17. The portable active drainage system as described in claim 1, wherein the reservoir port includes a one-way valve, the one-way valve maintaining the vacuum inside the vacuum chamber during removal or replacement of the reservoir.

18. The portable active drainage system as described in claim 1, wherein the vacuum source moves gases from the vacuum chamber into the atmosphere.

19. The portable active drainage system as described in claim 18, wherein the vacuum port includes a one-way valve, the one-way valve maintaining vacuum inside the vacuum chamber during an interruption in the vacuum source.

20. The portable active drainage system as described in claim 1, further comprising:

a second drainage tube port, wherein fluid is vented from the animal through the second drainage tube port when the second drainage tube port is connected to a second drainage tube extending from a location inside the animal.

21. A method for draining fluid from a mammal, the method comprising the steps of:

inserting a chest tube into the pleural cavity of a mammal so that a first end of the chest tube is proximate to a lung;

connecting a second end of the chest tube to an active drainage system;

applying a vacuum from the active drainage system to the chest tube;

regulating the vacuum to correspond to an air leak in the lung; and venting fluid from a location proximate to the lung while the mammal ambulates and while the mammal supports the weight of the active drainage system.

22. The method for draining fluid from a mammal as described in claim 21, the method comprising the further step of:

determining an amount of air leak in the lung with a flow meter of the active drainage system.

23. The method for draining fluid from a mammal as described in claim 21, the method comprising the further step of:

regulating the vacuum so that it does not harm living tissue proximate to the first end of the chest tube.

24. The method for draining fluid from a mammal as described in claim 21, wherein the mammal is a human.

25. A portable active drainage system comprising:

vacuum generating means for generating a vacuum;

power source means for supplying an electric current to the vacuum generating means;

venting means for directing vacuum from the vacuum generating means to a drainage tube extending from a location inside an animal and for venting fluid from the animal;

separating means for separating liquid and gas from the vented fluid;

collection means for collecting the separated liquid; and support means permitting the animal to support the weight of the portable active drainage system while ambulating.

* * * * *